(12) United States Patent
Attia

(10) Patent No.: US 10,000,618 B2
(45) Date of Patent: Jun. 19, 2018

(54) POLYMERIC AEROGEL FIBERS AND FIBER WEBS

(71) Applicant: Yosry A. Attia, Delaware, OH (US)

(72) Inventor: Yosry A. Attia, Delaware, OH (US)

( * ) Notice: Subject to any disclaimer, the term of this patent is extended or adjusted under 35 U.S.C. 154(b) by 25 days.

(21) Appl. No.: 15/362,058

(22) Filed: Nov. 28, 2016

(65) Prior Publication Data

US 2017/0073491 A1 Mar. 16, 2017

Related U.S. Application Data

(63) Continuation-in-part of application No. 14/700,387, filed on Apr. 30, 2015, now Pat. No. 9,512,286, and a continuation of application No. 13/483,475, filed on May 30, 2012, now Pat. No. 9,034,934, and a continuation of application No. 14/727,905, filed on Jun. 2, 2015, now Pat. No. 9,540,495.

(51) Int. Cl.

| | | |
|---|---|---|
| *C08J 9/28* | (2006.01) | |
| *C08J 9/36* | (2006.01) | |
| *C08J 9/00* | (2006.01) | |
| *A61K 9/48* | (2006.01) | |
| *A61K 31/75* | (2006.01) | |
| *B01J 20/26* | (2006.01) | |
| *B01J 20/28* | (2006.01) | |
| *C11D 7/24* | (2006.01) | |
| *C11D 7/32* | (2006.01) | |
| *D03D 15/00* | (2006.01) | |

(52) U.S. Cl.
CPC .............. *C08J 9/28* (2013.01); *A61K 9/4825* (2013.01); *A61K 9/4833* (2013.01); *A61K 9/4866* (2013.01); *A61K 9/4891* (2013.01); *A61K 31/75* (2013.01); *B01J 20/261* (2013.01); *B01J 20/262* (2013.01); *B01J 20/28004* (2013.01); *B01J 20/28023* (2013.01); *B01J 20/28038* (2013.01); *C08J 9/0061* (2013.01); *C08J 9/0066* (2013.01); *C08J 9/365* (2013.01); *C11D 7/241* (2013.01); *C11D 7/3263* (2013.01); *D03D 15/00* (2013.01); *C08J 2201/026* (2013.01); *C08J 2201/0502* (2013.01); *C08J 2201/0524* (2013.01); *C08J 2205/024* (2013.01); *C08J 2205/026* (2013.01); *C08J 2205/028* (2013.01); *C08J 2207/10* (2013.01); *C08J 2323/06* (2013.01); *C08J 2323/12* (2013.01); *C08J 2423/08* (2013.01); *C08J 2427/16* (2013.01); *C08J 2427/20* (2013.01); *C08J 2431/04* (2013.01)

(58) Field of Classification Search
CPC .... A61K 31/75; A61K 9/4825; A61K 9/4833; A61K 9/4866; A61K 9/4891; B01J 20/261; B01J 20/262; B01J 20/28004; B01J 20/28023; B01J 20/28038; C08J 9/0061; C08J 9/0066; C08J 9/28; C08J 9/365; C08J 2201/026; C08J 2201/0502; C08J 2201/0524; C08J 2205/024; C08J 2205/026; C08J 2205/028; C08J 2207/10; C08J 2323/06; C08J 2323/12; C08J 2423/08; C08J 2427/16; C08J 2427/20; C08J 2431/04; C11D 7/241; C11D 7/3263; D03D 15/00
See application file for complete search history.

(56) References Cited

U.S. PATENT DOCUMENTS

| | | | | | |
|---|---|---|---|---|---|
| 4,873,218 | A | * | 10/1989 | Pekala | ............. B01J 20/20 502/418 |
| 5,476,878 | A | * | 12/1995 | Pekala | ............. B01J 13/0091 521/181 |
| 6,087,729 | A | * | 7/2000 | Cerofolini | ............. C08F 292/00 257/759 |
| 9,109,088 | B2 | * | 8/2015 | Meador | ............. C08G 73/101 |
| 2006/0116433 | A1 | * | 6/2006 | Lee | ............. B29C 67/20 521/142 |
| 2008/0287561 | A1 | * | 11/2008 | Menashi | ............. C08J 9/0066 521/142 |

* cited by examiner

*Primary Examiner* — Irina S Zemel
(74) *Attorney, Agent, or Firm* — Mueller Law, LLC; Jerry K. Mueller, Jr.

(57) ABSTRACT

Disclosed is a method for making a polymer or copolymer aerogel product by forming an aerogel polymer or copolymer solution in the presence of a polymer or copolymer catalyst and solvent therefor. The aerogel polymer or copolymer solution is drained onto a spinning disk or cup. The solvent is removed under aerogel forming conditions to produce the aerogel fiber web or yarn product.

17 Claims, 1 Drawing Sheet

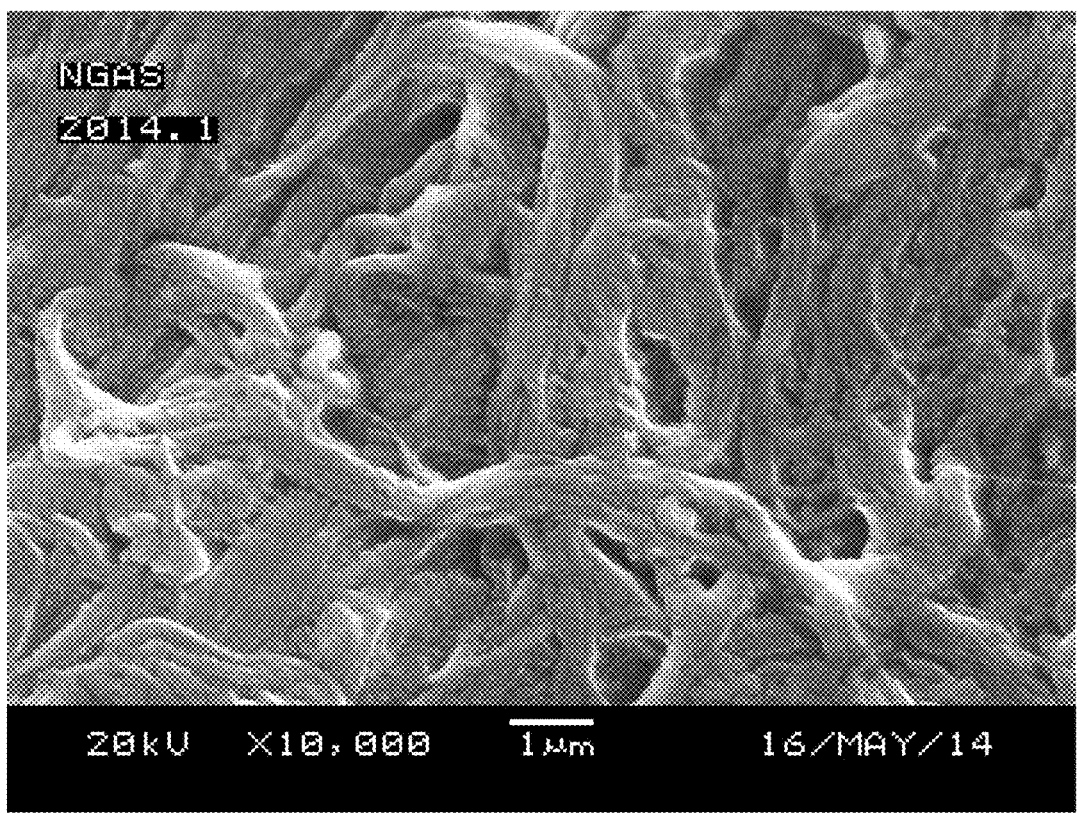

POLYMERIC AEROGEL FIBERS AND FIBER WEBS

CROSS-REFERENCE TO RELATED APPLICATION

This application is a continuation of U.S. Ser. No. 14/727,905 filed Jun. 2, 2015, which is continuation-in-part of U.S. Ser. No. 14/700,387 filed Apr. 30, 2015, which is a division of U.S. Ser. No. 13/483,475 filed May 30, 2012, now U.S. Pat. No. 9,034,934; and claims benefit of U.S. provisional application Ser. No. 62/141,917, filed on Apr. 2, 2015, the disclosures of which are expressly incorporated herein by reference.

STATEMENT REGARDING FEDERALLY SPONSORED RESEARCH

Not applicable.

BACKGROUND

Aerogels are three-dimensional network of nanophase architecture composed of gas [usually air] and solid structure, with air [gas] to solid ratio of up to 99% by volume. Thus aerogels have high porosity, high specific surface area, and very low density. The entrapped motionless air [gas] in the pores is responsible for the high insulation [low thermal conductivity] of the aerogel materials. Aerogels can be made as large monolithic shapes, or micron/submicron size bodies, or any size and shape in between. The gas inside the aerogel nanostructures can be replaced [displaced] with other substances, such as, for example, pharmaceuticals, which then are released into the desired targets in a controlled manner.

Polyethylene is a non-polar material with many desirable properties. At ambient conditions, it is considered rather chemically inert, non-toxic, transitive of infrared [IR] radiation, outstanding electrical insulating properties, such that its dielectric constant, and power factor are almost independent of frequency and temperature. It has also desirable mechanical properties.

Research, conducted to explore the possibility of preparation of novel polyethylene only aerogel materials, managed to create a novel methodology to manufacture polyethylene aerogels, which included preparation of polyethylene aerogels using standard polyethylene polymers [low and medium molecular weight (MW)] as aerogel precursors. Research proceeded to further develop this material to comply with multiple specifications [including radiometric, mechanical, thickness, as well as several other requirements]. It was then realized that preparation of thin [2-3 mm] and ultrathin [0.5-0.9 mm] aerogel sheets (using the standard polyethylene polymers), which is necessary for packaging of electronics, compromised radiometric and mechanical properties of the aerogel sheet. To solve this shortcoming, the research efforts obtained high density [HDPE] and ultrahigh molecular weight [UHMW] polyethylene polymeric precursors and proceeded to develop polyethylene aerogel sheets from these precursors to meet all the specifications and performance requirements for electronics and sensors applications.

These newly developed polyethylene aerogels may be considered as a platform technology for many other applications, including thermal, cryogenic, and sound insulation; sound frequency modulation, computer electronics, wide band antennas, membrane separations, filtration, as well as controlled release of encapsulated substances. Several product specifications, and performance criteria, such as mechanical, radiometric, insulation, and suitability for packaging of electronics, were met with outstanding results.

Broad Statement

Polyethylene aerogels and aerogel fiber webs or fabrics (woven or non-woven) have a high degree of molecular alignment and interconnected fibers, which offer good mechanical strength and high porosity with open interconnected three-dimensional pore structure of the aerogel fibers. The high porosity of the aerogel fibers forming the web, offer a distinct advantage over solid fibers and fiber webs formed from polymer melts, or other non-gel form of polymer solutions. In this procedure, the polymer in solution is made into cross-linked gel with three-dimensional open pore structure before introducing it to the fiber web making process.

The polymer or copolymer aerogel may be a polyolefin, polyester, polyamide, etc. The polymer or copolymer aerogel may be in the form of a fiber, optionally twisted for form a yarn. A web of such fibers forms a fiber web or fabric.

BRIEF DESCRIPTION OF THE DRAWINGS

For a fuller understanding of the nature and advantages of the present method and process, reference should be had to the following detailed description taken in connection with the accompanying drawings, in which:

FIG. 1 is a photomicrograph of the PE-2M aerogel fiber web of Example 1.

The drawing will be described in greater detail below.

DETAILED DESCRIPTION

Desired Polyethylene Aerogel Properties Include

High thermal insulation [low thermal conductivity; in the range of 5-45 mW/m-K];

Integral and uniform micro and macro physical structure with adequate mechanical strength for handling;

The ability to produce very thin sheets [1-3 mm], and ultra-thin sheets [0.1-1.0 mm] encompassing 1 & 2 above;

Good radiometric properties, such that high radiation transmission through the aerogel is not impeded by reflection, scattering, or absorption of such radiation;

Ability to reversibly stick to other materials or other aerogel sheets in electronic packaging; and High electric sheet resistance.

AEROGEL PREPARATION STRATEGY:

1-Gelation Mechanism:

Polyethylene is soluble in hot hydrocarbon solvents, such as, for example, toluene and benzene, but insoluble at ambient room temperature. The dissolution temperature of polyethylene in toluene increases with the starting polymer molecular weight. Dissolved polymer molecules in solution are then bridged together to form a three dimensional network that entrap the solvent inside them [i.e., liquid gel], which upon cooling to ambient temperature, becomes solid gel of polymer network enclosing liquid toluene solvent inside the pores. On removal of the liquid solvent from the gel network, the solvent is replaced with a gas [air or $CO_2$ gas for example] and forms a dry polyethylene aerogel.

Polymer gelation bridging is accomplished by a peroxide catalyst, such as, for example, benzoyl peroxide that causes free radical reactions between the polymer molecules, when activated by heat or ultraviolet radiation energy. The overall reactions are believed to be as follows:

1—Peroxide catalyst activation:

ROOR[e.g., benzoyl peroxide]+heat or UV light=2RO·[active free radical catalyst]

2—Initiation/polymer activation:

Polymer solution(2P)+Peroxide(2RO$_2$·)=2P·+2RO+H$_2$(gas)

3—Polymer-polymer bridging–Free radical termination:

2P·=(P–P)$_n$ bridged polymer network

4—Catalyst decomposition:

2RO+heat[or UV light]=2CO$_2$(gas)+2Benzene

5—Hydrogen consumption:

H$_2$+0.5O$_2$(air)=H$_2$O.

6—Overall polymer-polymer bridging gelation Reaction:

ROOR+2P+heat[or UV light]=(P–P)$_n$ polymer gel+CO$_2$(gas)+H$_2$O+2Benzene.

7—Gelation reactions by-products, benzene, water are removed from gel during supercritical drying, while CO2 gas is released to atmosphere during gelation.

The duration of the active free radical catalyst is determined by the number of half life cycles [half-life is the time required to decompose 50% of remaining catalyst in solution]. It is believed that 97% of benzoyl peroxide is decomposed after five (5) half-life cycles, and 99% decomposed after (7) seven half-lives. Half-life temperatures are: 10-hours at 73 C.°; 1-hour at 92 C.°; and 1-minute at 131 C.°. Thus, at a gelation reaction temperature of 130 C.°, 99% of catalyst is decomposed after about 7 minutes of reaction.

2—Thermal Insulation & Radiation Absorption:

Production of low-density aerogel would achieve both (a) low absorption of IR radiation, since absorption is a function of weight, (b) as well as increase thermal insulation due to higher pore volume/volume porosity. The goal of thermal insulation performance of these aerogels is to achieve a thermal conductivity, [K] in the range of 5-45 mW/m-K.°.

3—Mechanical Strength:

From gelation equations, control of humidity in air and solvents and chemicals involved in the gelation process is vital to achieving more complete gelation linkages and better mechanical strength. Also, higher molecular weight polymers would afford more linkages and lead to better mechanical strength aerogels.

4—Thin and Ultra-Thin Aerogel Sheets:

These would be possible if 2 & 3 above are achieved.

5—Reflection and Scattering Minimization:

Reflection of radiation by polyethylene aerogels dried at pressures lower than 1300 psi was minimized by the use of solvent exchange with acetone, an anti-solvent for polyethylene. Polyethylene aerogels treated with the acetone anti-solvent prior to drying had excellent radiometric performance, e.g., very low reflectance, compared with those not treated with anti-solvent.

However, it was observed that improved radiometric characteristics of the 2 million MW polyethylene aerogels also was achieved by implementing better supercritical drying techniques at higher pressures [over 1500 psi] and lower temperatures as shown in Table 8.

A possible mechanism of lowering reflection of polyethylene aerogel using anti-solvent is believed to be through formation of nano-sized "bumps" or precipitates on the aerogel structure. These nano-size "bumps" are smaller than the light's wavelength, so that the surface acts as having a continuous refractive index gradient between air and the aerogel, which decreases reflection by effectively removing the air-aerogel interface.

Another possible factor is the removal of toluene from the gel through solvent exchange with acetone, and higher solubility of acetone in supercritical CO$_2$ fluid, leading to more thoroughly dried aerogel with minimal toluene residues.

6—Reversible Adhesion and Shrinkage Elimination of PE Aerogels:

This was a chance discovery from enhanced supercritical carbon dioxide drying of gels using higher pressure than "standard" practice, which also minimized or eliminated shrinkage of gels during drying.

Aerogel Fiber Web

Aerogel fiber webs have a high degree of molecular alignment and interconnected fibers, which offer good mechanical strength and high porosity with open interconnected three dimensional pore structure of the aerogel fibers. The high porosity of the aerogel fibers forming the web, offer a distinct advantage over solid fibers and fiber webs formed from polymer melts, or other non-gel form of polymer solutions. In this procedure, the polymer in solution is made into cross-linked gel with three-dimensional open pore structure before introducing it to the fiber web making process. Gel fiber web is made by discharging the hot gel solution from the reactor, on to a high speed centrifugal spinning disc, which distributes the gel in thin fibrous spray sheet on to a collection vessel lined with a gel support sheet. The collection vessel moves up and down with a computer controlled motion sensor and actuator. The gel-laden support sheet is then dried to extract the solvent, by either supercritical [autoclave] method, or by air-drying of solvent, to produce dry aerogel fiber web. The aerogel fiber web may be used directly, or may be converted into yarns, by twisting the web with a spindle type technique. The yarns may then be used for weaving fabrics.

Polyethylene [PE] aerogel fiber webs measuring between about 1.5-1.8 meters long by about 22-25 centimeters wide, and different thicknesses ranging from about 0.1 mm up to 0.5 mm or more in thickness have been developed and prepared in TAASI laboratory. The web sheets are very flexible, durable, dust resistant, and rather chemically inert and non-toxic at ambient and cold temperatures.

The PE aerogel fiber web is hydrophobic [water repellent], and is ideal for cold temperature and cryogenic insulation. Optionally, the web can be augmented with other materials such as, for example, Nylon, polyester, etc., to impart other desirable properties, for example, the web can be made both oil repellent and water repellent at the same time.

Electrical insulation properties of polyethylene are outstanding. Both its dielectric constant and power factor are almost independent of frequency and temperature.

APPLICATIONS OF AEROGEL FIBER WEB

THERMAL INSULATION: textiles, electronics, oil pipelines, appliances, natural gas & oil transport tankers, buildings, cryogenics, food, biomedical [organ transfer, vaccines, medicines], etc.

SOUND INSULATION & ACCOUSTICS: sound labs, recording studios, stereo speakers, sound modulations, etc.

ELECTRIC INSULATION: cable insulation, electronics, etc.

ABSORBANCE: Absorption and adsorption of hydrophobic substances such as oils and fatty acid soaps and bile with potential applications in healthcare and beauty products, cleaning of oil spills, etc.

ENCAPSULATION: absorbents, catalysts, fragrance, drugs, etc.

SEPARATION MEMBRANES: Gas filtration, nano-size and micro-size separations.

BIO-MEDICAL: Tissue engineered scaffolds [nerve, muscle, and tendons], wound dressings & healing, cell adhesion & proliferation.

DRUG DELIVERY/CONTROLLED RELEASE: Drugs, biologics, nutraceuticals, etc.

PERFORMANCE

THERMAL INSULATION: Thermal insulation is measured by the thermal conductivity factor: k in milli-Watts per meter thickness per degree Kelvin; thus, the lower thermal conductivity factor [k], the higher is the insulation performance. Measured thermal conductivity of some PE-aerogel fiber webs are shown below:

2-layer web: k)(mw/m*K.°)=14.63 at 21 C.°; and 20.22 at 24 C.°.

3-layer web: k)(mw/m*K.°)=9.16 at 8 C.°; 10.44 at 18 C.°; 17.3 at 23 C.°; 22.7 at 26 C.°.

ABSORPTION: Laboratory tests showed that:

7.2 grams of cooking oil can be absorbed/adsorbed by 1.0 gram of PE-aerogel fiber web.

15.0 grams of bile solution can be absorbed by 1.0 gram of PE-aerogel fiber web. Aqueous soap/detergent solutions also are expected to be absorbed by the polyethylene aerogel fiber web.

No absorption of pure water.

OPTICAL QUALITY: PE aerogel fiber webs are normally opaque white, but almost transparent. PE aerogel fiber webs with 93-97% light transmittance were prepared in the laboratory. Thus, transparent and opaque aerogel fibers and fiber webs may be prepared.

ENCAPSULATION: Several types of particulates have been successfully encapsulated in the PE-aerogel fiber web with no dusting. Encapsulated particulates include Nano-diamonds, silica aerogel, Pristina™ tri-cat aerogel catalyst, and Pristine™ ST-31 adsorbent. There is no reason to doubt that other substances similarly can be encapsulated in the aerogel fiber web.

PROPERTIES: Aerogel density can be prepared to range from about 0.01-0.1 g/cc, but typically range from about 0.02-0.05 g/cc; with volume porosity ranging from about 90% up to 99% volume.

Process variables tested include, for example, polymer type, polymer concentration, spinning speed, flow rate of hot gel solution onto spin disc, temperatures of reaction, and fiber making procedure.

Tested polymer types include: polyethylene (PE) of average molecular weight (MW)=two million [PE-2M] and half million [PE-0.5M]; polypropylene [PP-0.34M]; ethylene-vinyl alcohol copolymer [PEVA]; polyvinyl acetate [PVAC-0.5 m]; polyvinylidene fluoride [PVF-0.53 m]; polyvinylidene fluoride-co-hexafluoropropylene [PVF-CO-HFP-0.455 m]; polyester=polyethylene terephthalate [PET-0.5 m]; and nylon-12. Polyethylene may be used as the main ingredient with other polymers added to impart special features or the other polymers might be used alone for forming aerogel fibers, yarns (twisted fibers), or fiber webs. Of particular interest are polyester and polyamide aerogel fibers, fiber webs, and yarns.

Polymer concentration tested ranged from between about 1-gram polymer per one liter of solvent, to about 4 grams polymer per liter solvent with the lower concentration of about 1-gram polymer per liter was found to be the optimum concentration.

Spin disc speed was varied between 3000 to 9000 rpm with 7000 rpm was the optimum speed.

Expanded Aerogel Encapsulating Particulates

Fighting Obesity: Arresting body weight gain and starting body weight loss. By reducing bile cholic acids and cholic acid salts below critical micelle concentration with aerogel encapsulating particles, much of the lipids [fats] and fatty foods would not be assimilated and accumulated in the body, but would be passed out undigested in feces.

Reducing fatty food intake has many potential benefits besides arresting weight gain, as excess fats interfere with many bodily functions which cause conditions such as type-2 diabetes, high blood pressure, blockage of arteries leading to cardiac arrest, liver malfunction, sleep disorder, bladder disorder, and so on.

Lowering Body Cholesterol: As bile is captured and removed by aerogel encapsulating particles, more cholesterol is used up in manufacturing bile cholic acids and salts, thus lowering cholesterol levels.

Colon Cancer Prevention: Bile acids are carcinogens and tumor promoters. Their role in carcinogenesis is documented in Barret's esophagus and adenocarcinoma at the gastro-esophageal junction. Thus, lowering levels of excess bile would help prevent colon cancer, as well as all forms of intestinal cancer that are similarly caused or aggravated by excess bile.

Treatment Of Chronic Diarrhea: Excess bile acids in the colon are a cause of chronic diarrhea, thus reducing or eliminating excess bile acids with aerogel encapsulating particles, should help combat this condition.

Polyethylene aerogel either alone or mixed with SCM [silica-calcium-magnesium]aerogel granules, encapsulated in pharmaceutical grade gelatin capsules with an enteric coating is useful for absorbing bile in situ. These aerogel materials have several special properties that make them uniquely suitable for the capture and removal of bile acids and salts. For example, they have high surface area, high porosity [up to 95% by volume or higher], and pore sizes largely in the macro-pore size [up to 80-85%] with the balance in the mezo and micro pore size ranges. This makes this aerogel material ideal for accommodating large molecules, such as cholic acids, into its interior. In addition, the calcium and magnesium sites are suitable for chemical binding of cholic and fatty acids.

The aerogel granules are delivered in enterically coated capsules to the small intestine [duodenum], where the bile is secreted for extraction of nutrients from foods. The aerogel granules are released from the capsules in the duodenum, and start absorption of the bile, transporting it with undigested foods, through the colon and out with the feces.

An enteric coating protects the aerogel particles from stomach acids and the environment for around a 2-hour duration in the stomach. These capsules rapidly disintegrate or burst [thus releasing the aerogel granules] and ultimately dissolve within 20-30 minutes in the less acidic, more basic environment of the small intestine. This type of enteric capsules has been studied and documented in scientific and commercial literature. An example study documenting enteric coating of capsules and confirming their function in vitro and in vivo [humans] testing is: "In Vitro and in Vivo Evaluation of Hydroxypropylmethyl Cellulose Phthalate Capsules", E. O. Cetin et al.; international journal of drug delivery, 3 (2011) 279-285.

Examples of commercially available enteric capsules are described by Xinchang Autoco Capsule Co. Ltd. [www.autoco.com.cn]; and colorcon company/xtendlife [www.xtendlife.com].

Dosage Calculation:

For assimilation of fatty foods into the body, the concentration of bile acid salts has to be higher than needed for the formation of micelles [i.e., critical micelle concentration, "CMC"]. Thus, to stop this assimilation, the concentration of bile acid salts in the small intestine should be lower than the critical micelle concentration.

This is accomplished by capture/absorption of excess bile acid salts with the disclosed enteric-coated aerogel capsules. To develop dosage guideline, one needs knowledge and data for (a) bile CMC, (b) bile production levels, and (c) sorption capacity of bile-sorb aerogel.

Critical Micelle Concentration (CMC): K. E. Heppert et al., [Current Separations Journal, 17:2 (1998)], reported critical micelle concentrations for primary bile acid salts as follows:

Sodium cholate [mw=430.6 gram/mol]: CMC=13-15 mm [5.6-6.5 g/liter, or 0.56-0.65%];

Sodium deoxycholate [mw=414.4]: CMC=4-6 mm [1.66-2.5 g/liter, or 0.166-0.25%]; and Sodium taurocholate [mw=537.7]: CMC=10-15 mm [5.38-8.07 g/liter or 0.54-0.81%].

Production of Bile Acid Salts:

Davidson et al. [Bile Acid Production in Human Subjects, Journal of Lipids Research, vol. 27 (1998)], reported clinical studies at Rockefeller University Hospital on a number of human patients. These studies measured daily acid synthesis by chemical analysis in 8 studies, and calculated the mean daily acid secretion at 0.8±0.2 mmol/day, or 10.4±2.8 µmol/kg per day.

If an average MW (molecular weight) of the three primary acid salts above is taken as 460.9, the daily production of acid salts for a 100 kg human body according to Davidson et al., will be 461 mg [0.461 g/day]

Sorption Capacity Of Bile-Sorb™ Aerogel: Laboratory Tests And Data:

In preliminary laboratory tests, 4.5 grams of bovine bile salts powder [Sigma-Aldrich] were dissolved in 100 ml distilled water, and the pH adjusted to 5.0. About 2.02 grams of SCM aerogel powder [Bile-Sorb] were mixed in the bile solution for 30 minutes, and then were filtered off. Residual bovine in solution was analyzed by evaporating water and weighing residual solids.

Test results indicated that 98.8% of the initial bovine bile acid salts were captured/absorbed by the aerogel powder, thus indicating that about 2.21 grams of bile salts can be captured and removed from solution by 1 gram of aerogel powder [i.e., thus the preliminary loading rate is 2.21 g bile salts per 1.0 gram of aerogel].

Dosage Guideline:

From the above data, it should be possible to lower cholic acid salts concentration to below CMC with about 2-grams of the aerogel particles per day. The aerogel powder is packaged in capsules at the rate of 150 mg aerogel per capsule.

For treating a 100 kg [224 lb.] Human, 4 capsules taken orally 30 minutes before each meal or a snack, three times per day [total 12 capsules, 1.8 grams], could be a starting point.

DETAILED PREPARATIONS AND EXAMPLES

Procedure for Polyethylene Aerogel Production/Preparation

Preparation/production of polyethylene aerogels involves the following tasks:

Preparation and casting of gel solution.

Removal of excess free solvent from gel [optional].

Anti-solvent treatment of gels [optional].

Removal of entrapped solvent from gel to produce dry aerogels.

Preparation and Casting of Polyethylene Gel Solution:

1-1: Polymer Dissolution:

In a typical preparation procedure, polyethylene solid powders or beads are dissolved in hot toluene solvent under reflux while being mechanically stirred in a glass pressure reactor. Electric heating tapes wrapped around the outside of the reactor and covered with an insulating sheeting material heat the reactor used in the laboratory preparations. The heating tape was controlled by a temperature controller, which was set at a predetermined temperature. Dissolution temperature was higher for higher molecular weight [MW] polymers and was around 130 C.° for 2-6 million MW. Dissolution was continued until a clear polymer solution was obtained. The amount of polymer dissolved varied from less than 1% wt. for ultrahigh molecular weight [UHMW] to 10% or higher for low MW polymers, depending on desired final aerogel properties [for example, density & porosity] to be achieved.

1-2: Addition of Gelation Catalyst:

Gelation catalyst used in laboratory preparations was benzoyl peroxide, which was supplied at about 50% wt. powder mixture with phthalate to avoid explosive hazard during shipping by air. Warm/hot benzoyl peroxide solution was made by dissolving predetermined amounts in toluene and heated to a warm temperature. The amount of benzoyl peroxide was varied between 2-20% of the polyethylene polymer weight, but it was selected at the equivalent of 10% wt [20% including the phthalate powder] of the polyethylene weight for almost all of the preparations, unless stated otherwise. The catalyst solution was added to the clear polymer solution while mixing was continued under reflux at set temperature for 10 minutes, unless otherwise stated. The reaction product was the gel solution, which remained clear at the reaction temperature.

1-3: Casting Gel Solution:

Hot gel solution was poured out of the reactor by opening the reactor bottom valve into heated and leveled metal (stainless steel plate on aluminum base) or glass molds. All molds had glass covers with a center hole to allow reactor valve tube access to mold but keep hot solvent vapors from escaping. All heating and mixing units were switched off and gel was allowed to cool down in mold to room temperature. On cooling gel converted from solution to solid wet gel.

Removal of Free Excess Solvent from Gel:

Small amounts of excess free solvent that are not part of the gel structure [entrapped inside gel network] are removed from cooled gel body/sheet in the laboratory preparations by one or more of the following methods:

Draining of solvent from casting mold;

Partial air-drying at ambient conditions [slow evaporation];

Partial forced air-drying at elevated temperatures [fast evaporation];

As discussed later, the need for this step may not be needed in future, as improvements in gel solution preparation are achieved to minimize or eliminate the presence of excess free solvent.

Anti-Solvent Treatment of Gels:

In an effort to improve the IR-radiometric properties of the polyethylene aerogels with regards to minimizing radiation reflection, the wet gels were treated with an anti-solvent. In this case, the anti-solvent of choice was acetone. Thus, the toluene-loaded gels were either transferred to and soaked in a bath of acetone for a period of time [0.5-2.0 hours], or sprayed in mold with acetone and kept soaking for a period of time. The resultant gels became snow white, and were taken to the final drying step.

Removal of Entrapped Solvent from Gel to Produce Dry Aerogel:

Wet gels were dried by both subcritical methods including ambient and forced air drying, and supercritical carbon dioxide solvent exchange in an autoclave. Tables 1-4 show both the aerogel preparation conditions and the resulting characteristics of those aerogels. The role of supercritical drying [and suggested further improvements] on the various properties of polyethylene aerogels are discussed later.

Results and Discussion:
Production of Polyethylene Aerogels:

Tables 1-8, show that polyethylene aerogels can be prepared by the methods described herein, with a range of performance characteristics. For example: aerogel density ranges from 0.6 g/cc to 0.01 g/cc or less; volume porosity range from 40% to over 99%; pore volume from 0.86 to over 80 cc/g; thickness from over 10 mm to less than 0.3 mm and all the way down to 0.007-0.028 mm [Gossamer aerogels]; mechanical properties from brittle, to tough, to very flexible; radiometric from unacceptably high reflectance, absorption, and scattering to very low values and excellent performance.

Additional properties achieved by discovery include polyethylene aerogel sheets with silky smooth feel and strong but reversible static cling, which obviated the need to use adhesives/glues to stick layers of sheets materials together in the packaging of electronic and sensor assemblies and, thus, improving overall performance and costs.

In achieving these results, many parameters and variables were identified, investigated and in many cases optimized. The main example parameters include:

Role of Humidity on Mechanical Strength of Polyethylene Aerogel:

Recognition of the possible deleterious effect of relative humidity in laboratory air and in solvents and chemicals used in preparation was made in early work with several attempts to add dehydrating reagents to ingredients in preparations but without much success. Finally, in later work, the use of anhydrous toluene, chemicals, and keeping laboratory air to below 40% [30-35%] at moderate room temperatures below 26 C.°. By avoiding humidity, the aerogels became much less brittle.

Role of Precursor Polymer Molecular Weight:

The results show that high [up to 1 million] and ultra high [2 million and above] polymer molecular weights are instrumental in improving mechanical strength, and making possible preparation of very thin aerogel sheets. In addition radiation scattering was improved.

3—Role of Anti Solvent on Radiometric Performance:

A chance discovery based on a hypothesis that polyethylene reflectance can be reduced by treating the wet toluene-laden gel sheets [or other shapes] in polyethylene anti-solvent, such as acetone, to exchange with and replace toluene in the gel structure. The first observation in the laboratory that acetone had an "opaquing, reflection lowering" effect on polyethylene [2million] was made when the wet gel sheet turned "snow white" on soaking in acetone bath for 1-2 hours.

However, the first successful preparation of 2M polyethylene aerogel sheet was made in later research, where marked improvement in aerogel reflection was made, compared with same aerogel made in earlier work, which was not treated with anti-solvent fluid exchange. All polyethylene aerogels thereafter were treated with acetone anti-solvent before drying with supercritical carbon dioxide. Table-5 shows examples of radiometric properties of polyethylene aerogels with and without anti-solvent treatment.

Role of Aerogel Density:

As expected, the results show that lowering aerogel density lowered radiation absorption, improved pore volume and porosity and, thus, improved insulation performance as well.

Role of Gel Drying Method:
Subcritical & Ambient Drying:

Table 1 A & B, show that subcritical and air drying can produce aerogels with a density range from 0.3-0.6 g/cc and a porosity range from 52% to 75%. Although subcritical including air drying methods can be used to completely remove the entrapped solvent to produce aerogels with adequate insulation performance, the micro physical structure is often non-uniform, and the mechanical and radiometric properties are far inferior to gels dried by supercritical carbon dioxide. Therefore, supercritical carbon dioxide solvent exchange was the method of choice for obtaining superior aerogels.

Drying with Supercritical $CO_2$ Fluid:

Supercritical drying did not automatically always yield expected results, however. It was thought that as long as supercritical conditions are employed, drying to perfect aerogels would result. Instead, gel shrinkage and other unexpected performance problems occurred. In later work, then, attention was paid to controlling the supercritical drying parameters, such as pressure, temperature, and continuous [dynamic] flow rate and time of supercritical carbon dioxide after the autoclave has achieved supercritical conditions. Thus, by increasing the pressure to 1400-1450 psi, at 35-37 C.°, and supercritical $CO_2$ flow for 20-30 minutes, no more shrinkage and superior products of 2M polyethylene aerogels were obtained. A similar observation on the beneficial use of higher pressure [1390 psi] than the normal 1250 psi with regards to shrinkage was made in earlier work, but its importance was not fully recognized at that time.

Relationship of Solubility of Solvents and Other Substances with Density of Supercritical Carbon Dioxide Fluid:

The importance of controlling supercritical pressure and temperature can be better understood by realizing that solubility of solvents, such as toluene, acetone, and alcohols, in supercritical carbon dioxide fluid is controlled by the density of the supercritical fluid, which is controlled by both the pressure and temperature. Therefore, better drying would be expected at the higher pressure and the corresponding temperature that enable the highest density of supercritical carbon dioxide [closer to the maximum of 0.8 g/cc].

Also, the amount of supercritical carbon dioxide fluid to completely dissolve the solvent [e.g., toluene, or acetone] is determined by the solvent's solubility [wt. %], and sufficient amount of supercritical $CO_2$ should be allowed to flow to achieve this.

Effect of Pressure and Temperature on Density of $CO_2$ Supercritical Fluid:

Table 6 shows the variation in density of supercritical carbon dioxide with pressure and temperature. These data were extracted from the $CO_2$ density-pressure phase diagram. From Table 6, it can be seen that in the pressure range 90-110 bar [1 bar=14.75 psi], there is almost a linear relationship between the change in density with pressure and temperature, while outside this pressure range, it is a non-linear relationship.

Effect of Pressure:

The density of $CO_2$ supercritical fluid ($\Delta D$) increases with increasing pressure ($\Delta P$) as follows:

$$\Delta D/\Delta P = 0.007 \pm (0.002) \text{g/cc/bar};$$

Thus for 10 bar increase, the density increase is 0.07 ($\pm 0.02$) g/cc.

Effect of Temperature:

The density of $CO_2$ supercritical fluid decreases with increasing temperature ($\Delta T$) as follows:

$$\Delta D/\Delta T = 0.0164 (\pm 0.0018) \text{g/cc/C.}°.$$

An empirical correlation between substance solubility change ($\Delta S$) with a change in pressure and temperature of supercritical $CO_2$ fluid is as follows:

$$S_2 = 1.7 \times (d_2/d_1) \times S_1 \quad [1]$$

where $S_2$=Solubility at the higher pressure, $S_1$=Solubility at the lower pressure, $d_2$=Density of $CO_2$ at the higher pressure, $d_1$=Density of $CO_2$ at the lower pressure.

Conversely, solubility at the lower pressure in relation to that at higher pressure is as follows:

$$S_1 = 0.59 \times (d_1/d_2) \times S_2 \quad [2].$$

In each case, the density is calculated to account for the effects of both the pressure and temperature.

Formation And Removal of Excess Free Solvent from Gel:

The presence of excess free solvent [not included in gel structure] is believed to be due to:

Use of reflux condenser during gelation, that returning condensed solvent [toluene] is excluded from participating in gel structure, and, Melting polymer gel at inside surfaces of reactor thereby releasing included solvent from its structure. Melting of polymer gel is a result of inefficient heat transfer from heating tape wrapped around reactor where the temperature is higher than the interior of gel solution, where the temperature is controlled. The amount of polymer lost for melting inside reactor is a function of gelation time, as shown in Table 7.

Approximately 20-29% of the initial polymer is lost to melting in 10 minutes of gelation, while, 54-61% is lost during 30 minutes, and about 65% is lost during 60 minutes of gelation time.

Removal of excess free solvent is made by partial air-drying methods as explained earlier. However, to prevent the formation of excess solvent in the first place, one or more of the following steps should be taken:

Design better heat transfer mechanism, such as circulating temperature controlled heating oil around reactor;

More efficient mixing to transfer heat from outside of reactor to interior of gel solution;

Employ shorter gelation time inside reactor, but continue gelation reaction in the heated casting mold;

Convert reflux condensation to a distillation function during gelation period, by letting evaporated solvent to condense outside reactor into a special container, but stop distillation before gel solution becomes more viscous than desired for casting;

Reduce heating temperature during gelation to 70-80° C. to avoid excessive evaporation of solvent but only as long as polymer gel solution remains clear without polymer precipitation.

TABLE 1-A

Preparations of "Low Density" Polyethylene Aerogels [MW: K = 1000, M = 1 million]

| Preparation Date | Polymer MW | Polymer Conc., wt % | Reaction Temp., C. | Drying Method | Remarks |
|---|---|---|---|---|---|
| 11/24/ | 135K | 10 | 75 | Air dry | |
| 11/23/ | 135K | 5 | 75 | Air dry + subcritical $CO_2$ @54 C. & 670 psi | |
| 10/10-19/ | 135K | 5 | 110 | Air dry + supercritical $CO_2$ @ 1350 psi & 52 C. | |
| 10/10-19/ | 35K (a) | 5 | 110 | Same as above | |
| 10/10-19/ | 35K (b) | 5 | 110 | Air dry only | |
| 6/27/ | 135K + 4K [80:20] | 10 | 130 | Supercritical $CO_2$ @ 1310 psi & 52 C. | |
| 6/27/ | 135K + 35K [80:20] | 10 | 130 | Same as above | |
| 6/27/ | 135K + 35K + 4K [80:10:10] | 10 | 130 | Same as above | |
| 9/28/ | 135K | 10 | 134 | Air dry, desiccator | 3" × 10" sheet, brittle |
| 9/30/ | 135K + 35K + 4K [80:10:10] | 10 | 130 | Same as above | [repeat 6/27/] |

TABLE 1-B

Performance Characteristics of Preliminary Polyethylene Aerogels

| Prepn. Date | Polymer MW | $T_h$, mm | D/L × W cm | $\rho_a$ g/cc | $V_p$ cc/g | $P_v$ % | [K] | [M] | [R] Remarks |
|---|---|---|---|---|---|---|---|---|---|
| 11/24/ | 135K | 6-9 | 3.8 | 0.46 | 1.45 | 63.5 | 20 | G/U | U Cracks, off white |
| 11/23/ | 135K | 5.7 | 5.7 | 0.30 | 2.49 | 74.9 | 20 | G | white, no cracks |
| 10/10-19/ | 135K | 6 | 5.8 | 0.12 | 7.65 | 90.24 | | G | |
| 10/10-19/ | 35K (a) | | 3.4 | 0.26 | 2.96 | 78.05 | | G | |
| 10/10-19/ | 35K (b) | | | 0.62 | 0.84 | 51.83 | | | |

TABLE 1-B-continued

Performance Characteristics of Preliminary Polyethylene Aerogels

| Prepn. Date | Polymer MW | $T_h$, mm | D/L × W cm | $\rho_a$ g/cc | $V_p$ cc/g | $P_v$ % | [K] | [M] | [R] | Remarks |
|---|---|---|---|---|---|---|---|---|---|---|
| 6/27/ | 135K + 4K [80:20] | 8.9 | 4.5 | 0.27 | 2.87 | 77.5 | | U | U | poor |
| 6/27/ | 135K + 35K [80:20] | 10 | 4.5 | 0.2 | 4.3 | 83.75 | | U | U | |
| 6/27/ | 135K + 35K + 4K [80:10:10] | 12 | 4.9 | 0.2 | 4.17 | 83.3 | | U | U | |
| 9/28/ | 135K | 10 | 7.6 × 25.4 cm | 0.17 | 5.19 | 86.17 | | U | | brittle |
| 9/30/ | 135K + 35K + 4K; 80:10:10 | 10 | 5.7 | 0.17 | 4.95 | 85.6 | | U | U | Broke to pieces |

Insulation: [K] = Thermal conductivity [mW/m-K °]; Mechanical [M] & Radiometric [R] performances: Good = G; Unsatisfactory = U, Excellent = E.
Pore Volume, $V_p$, Volume Porosity = $P_v$, Apparent Density = $\rho_a$, Thickness = $T_h$, Dimensions: D = Diameter: Length × Width = L × W.

TABLE 2A

PREPARATION OF HIGH DENSITY AND ULTRA HIGH MOLECULAR WEIGHT [UHMW] POLYETHYLENE AEROGELS

| Preparation Date | Polymer MW* | Polymer conc., wt % | Solution Temp., C. | Drying Methods | Anti-solvent treatment | Remarks |
|---|---|---|---|---|---|---|
| 9/11-14/ | 300K | 5 | 110 | $CO_2$ Supercritical @1280 psi & 49° C. | No | dehydrating agent used, washed before drying |
| 9/11-14/ | 300K | 5 | 110 | Same as above | No | No dehydrating agent added |
| 10/2/ | 300K | 5 | 176 F. | $CO_2$ subcritical @970 psi & 63 C. | No | |
| 10/2/ | 2M | 5 | 135 | Same as above | No | Some shrinkage in desiccator |
| 10/3/ | 6M | 5 | 135 | CO2 supercritical | No | |
| 11/9-12/ | 2M [3" × 10"] | 5 | 135 | Supercritical | No | ~50% shrinkage |

TABLE 2B

Aerogel Characteristics & performance

| Preparation Date | Polymer MW | $T_h$, mm | D/L × W cm | $\rho_a$, g/cc | $V_p$, cc/g | $P_v$, % | Remarks |
|---|---|---|---|---|---|---|---|
| 9/11-14/ | 300K | 6-8 | 4.2 | 0.075 | 12.50 | 93.75 | Good white monolith |
| 9/11-14/ | 300K | 6 | 3.2 | 0.097 | 9.48 | 92.0 | Good white monolith |
| 10/2/ | 300K | 10 | 4.9 | 0.096 | 9.58 | 92.0 | good |
| 10/2/ | 2M | 5 | 3.7 | 0.34 | 2.11 | 71.74 | Good, shrinkage, yellowish |
| 10/3/ | 6M | 13 | 4.7 | 0.124 | 7.23 | 89.67 | Very good |
| 11/9-12/ | 2M | 3 | 13.6 | 0.284 | 2.69 | 76.3 | Intact, pliable |

Pore Volume = $V_p$, Volume Porosity = $P_v$, Apparent Density = $\rho_a$, Thickness = $T_h$, Dimensions: Diameter = D; Length × Width = L × W.

TABLE 3A

PREPARATION OF ULTRAHIGH MOLECULAR WEIGHT POLYETHYLENE AEROGELS

| Preparation Date | Polymer MW | Polymer conc., wt % | Solution Temp., C. | Drying Methods | Anti-solvent? | Remarks |
|---|---|---|---|---|---|---|
| 12/10-11/ | 2M [3 × 10"] | 5 | 126 | supercritical + air dry | No | Shrinkage [7.75 × 2.5"] |
| 7/18/ | 2M [4 × 12"] | 2.5 | 126 | Subcritical @770 psi | No | |
| 9/6-11/ | 2M | 2.8 | 130 | Supercritical @1380 psi &56 C., 2 runs | No | Almost No shrinkage |
| 10/15-19/ *Anti-solvent treatment *Anhydrous Toluene use | 2M [19 × 8"] | 2.1 | 128 | Air + supercritical | Yes [30 min] | Transparent gel became white when soaked in anti-solvent. Shrinkage only after air dry to[10 × 5"] |
| 12/1-5/ | 2M [25" × 4"] | 2.0 | 130 | Air dry + supercritical | Yes | Shrinkage by air drying |
| 5/7-8/ | 2M [4 × 12"] | 2.14 | 130 | Air dry + supercritical | Yes | |
| 6/9-11/ | 2M [4 × 12"] | 1.7 | 126 | Air dry + supercritical @1280&42 C. | Yes | |
| 7/15-17/ | 2M [4 × 12"] | 0.96 | 129 | Air dry + supercritical @1290&45 C. + scCO$_2$ flow 6 minutes | Yes | Excellent very small shrinkage |
| 7/21-22/ | 6M [4 × 12"] | 0.95 | 129 | Air dry + supercritical @1290&45 C. + scCO$_2$ flow 6 minutes | Yes | Excellent no shrinkage |
| 8/5-6/ | 6M [4 × 12"] | 1.2 | 130 | Air dry + supercritical @1290&45 C. + scCO$_2$ flow 6 minutes | Yes | Very good |

TABLE 3B

Aerogel Characteristics & Performance

| Preparation Date | Polymer MW | $T_h$, mm | L × W cm | $\rho_a$, g/cc | $V_p$, cc/g | $P_v$, % | Remarks |
|---|---|---|---|---|---|---|---|
| 12/10-11/ | 2M [3 × 10"] | 7 | 19.7 × 6.35 | 0.195 | 4.3 | 83.79 | Very good |
| 7/18/ | 2M [4 × 12"] | 25 | 21.65 × 6.5 | 0.3 | 2.5 | 75 | good |
| 9/6-11/ * No Anti-solvent use | 2M | 17 | 4.5 | 0.34 | 2.11 | 71.86 | Good, but high reflectance |
| 10/15-19/ *Anti-solvent treatment *Anhydrous Toluene use | 2M [19 × 8"] | 4 | 24.13 × 6.35 | 0.417 | 1.57 | 65.26 | Very good mechanical and improved radiometric properties. Lower reflectance |
| 12/1-5/ | 2M [25" × 4"] | 3.5 | 24.77 × 11.43 | 0.40 | 1.67 | 66.68 | good |
| 5/7-8/ | 2M [4 × 12"] | 2.8 | 21.5 × 6.2 | 0.26 | 3.01 | 78.34 | Some shrinkage, good |

TABLE 3B-continued

Aerogel Characteristics & Performance

| Preparation Date | Polymer MW | $T_h$, mm | L × W cm | $\rho_a$ g/cc | $V_p$, cc/g | $P_v$, % | Remarks |
| --- | --- | --- | --- | --- | --- | --- | --- |
| 6/9-11/ | 2M [4 × 12"] | 1.0 | 27.5 × 9 | 0.097 | 9.17 | 91.67 | mech., not uniform Very white, uniform, flexible, best to date |
| 7/15-17/ | 2M [4 × 12"] | 4 | 27 × 8.5 | 0.043 | 22.43 | 96.44 | Excellent, flexible |
| 7/21-22/ | 6M [4 × 12"] | 2 | 29.6 × 7.9 | 0.037 | 26.2 | 96.94 | Excellent |
| 8/5-6/ | 6M [4 × 12"] | | | 0.047 | 20.45 | 96.10 | Very good |

TABLE 4A

Preparation of Very Thin And Ultrathin Polyethylene Aerogels

| Preparation Date | Polymer MW | Polymer Conc., wt % | Solution Temp., C. | Drying Method | Anti-solvent? | Remarks |
| --- | --- | --- | --- | --- | --- | --- |
| 8/12-14/ | 6M [0.9 mm] | 1.06 | 130 | Air [18 hr.] + supercritical | Yes | |
| 8/25-28/ | 6M [0.8 mm] | 1.3 | 131 | Air + autoclave + flow | Yes | |
| 10/9-10/ | 6M [Std] | 1.05 | 130 | Same as above | Yes | |
| 10/9-10/ | 6M [skin] | 1.05 | 130 | Same as above | Yes | Short air drying [<1 hr.] |
| 4/6-8/ | 2M | 0.71 | 133 | Air [12 hr] + supercritical | Yes [2 hr] | |
| 4/13-16/ | 2M | 0.7 | 127 | same | Yes | Squeeze Gel between 2 glass sheets |
| 4/14-16/ | 6M | 0.71 | 130 | Air [7 hr] + supercritical | Yes | Squeeze gel |
| 4/21-23/ | 6M | 0.71 | 130 | Air [7 hr] + supercritical | Yes | No squeeze |
| 5/26-27/ | 2M [Gossamer] | 0.71 | 130 | Air [1 hr warm hair dryer + 1 hr ambient] + supercritical | Yes | Squeeze |
| 6/30-7/2/ | 2M [std] | 1.09 | 128 | Air [5.5 hr] + supercritical | Yes | Some shrinkage |
| 7/7-10/ *Higher pressure, low temp [high density of sc $CO_2$] | 2M [std = 2.5 mm] | 0.9 | 129 | Air [7.5 hr] + supercritical @ 1400 psi & 35 C. | Yes | No shrinkage |
| 7/14-18/ | 2M [std] | 0.9 | 129 | Supercritical @ 1400 psi & 37 C. | Yes | Excellent No shrinkage |
| 8/26-28/ | 2M | 0.76 | 129 | Air [1 hr] + supercritical | Yes | Thin sheets stick to supports |
| 9/21-23/ | 2M | 0.48 | 129 | Air [40 min] + supercritical | Yes [40 min] | Simultaneous acetone spray and air dry, no squeeze, stick to support |
| Oct. 7-9, 2009 | 2M | 0.29 | 129 | Air [1.5 hr] + supercritical | Yes | |

TABLE 4B

Characteristics and Performance of Polyethylene Aerogels

| Preparation Date | Polymer MW | Thickness $T_h$, mm | Dimension L × W cm | Density $\rho_a$, g/cc | Pore volume $V_p$, cc/g | Porosity $P_v$, % vol | Remarks |
|---|---|---|---|---|---|---|---|
| 8/12-14/ | 6M | 0.94 [0.9 mm] | 29.33 × 9.03 | 0.16 | 5.42 | 87.2 | Good, not uniform |
| 8/25-28/ | 6M | 0.6 [0.8 mm] | 26 × 10 | 0.19 | 4.49 | 84.34 | good |
| 10/9-10/ | 6M [Std] | 3.8 | | 0.044 | 21.9 | 96.4 | Very flexible, excellent |
| 10/9-10/ | 6M [skin] | 1.03 | | 0.058 | 16.4 | 95.0 | Very flexible, excellent |
| 4/6-8/ | 2M | 1.2 | 30 × 8 | 0.061 | 15.84 | 95 | good |
| 4/13-16/ | 2M | 0.44 | 28 × 11 | 0.105 | 8.69 | 91.26 | Good, flexible |
| 4/14-16/ | 6M | 0.52 | 26 × 8.8 | 0.16 | 5.26 | 86.2 | Good, flexible |
| 4/21-23/ | 6M | 0.89 | 29.6 × 10.6 | 0.087 | 10.66 | 92.73 | Good, flexible |
| 5/26-27/ | 2M [Gossamer] [micro-thin] | 0.04 | 28.3 × 10.5 | 0.59 | 0.86 | 51 | Excellent mechanical, flexible, transparent |
| 6/1-3/ | 2M [Gossamer] [7-40 micron] | 0.02 [0.007-0.047] | | 0.76 | 0.48 | 45.0 | Excellent mechanical, flexible, transparent, |
| 6/30-7/2/ | 2M [std] | 2.1 [average] | | 0.075 | 12.5 | 94.0 | Flexible, very good |
| 7/7-10/ *Higher pressure, low temp [higher density of sc $CO_2$] | 2M [std = 2.5 mm] | 3.9 | 30.23 × 9.2 | 0.022 | 44.12 | 98.2 | Excellent very white, no shrinkage |
| 7/14-18/ | 2M [std] | 4.0 | 29.6 × 8.8 | 0.027 | 36.2 | 97.8 | Spectacular |
| 8/26-28/ * Tacky, self adhesive, static cling | 2M | 0.3 | | 0.069 | 13.66 | 94.25 | Very flexible, excellent, repeat Sep. 2-4, 2009 [tacky], static cling |
| 9/21-23/ *self adhesive, static cling | 2M | 0.5 | 27 × 11.1 | 0.044 | 21.9 | 96.3 | Tacky flexible, self adhesive |
| 10/7-9/ *self adhesive, static cling | 2M | 0.5 [±0.05] | 27.4 × 11 | 0.026 | 37.63 | 98.0 | Static cling, excellent, very soft, tacky feel, sticks to objects |

TABLE 5

Examples of Intrinsic Radiometric Characteristics of some Polyethylene Aerogels

| Preparation Date | Polymer MW | Thickness mm | Density g/cc | Remarks on Radiometric characteristics |
|---|---|---|---|---|
| 10/7-9/* | 2M | 0.5 | 0.026 | Excellent, Best ever |
| 7/7-10/* | 2M | 3.9 | 0.022 | Very good, Best to date |
| 10/15-19/* | 2M | 4.0 | 0.417 | Good improvement |
| 9/11/** | 2M | 4.2 [3.1-5.3] | 0.27 | Not good |
| 9/11-14/** | 300K | 6.0 | 0.097 | Not good |
| 10/2/** | 300K | 10.0 | 0.096 | Not good |

*Anti-solvent treatment applied;
**Anti solvent treatment NOT applied.
Radiometric Characteristics include: Absorption Coefficient, α/unit length; Back Scattering Coefficient, β; Forward scattering, δ; Reflection %.

TABLE 6

Density (g/cc) of supercritical Carbon dioxide at Various Temperatures and Pressures Derived from CO2 Density-Pressure Phase Diagram. [Maximum Density of Supercritical CO2 = 0.80 g/cc]

| Pressure, Bar [PSI]* | 32 C.° | 37 C.° | 40 C.° | 47 C.° | 57 C.° |
|---|---|---|---|---|---|
| 80 [1180] | 0.52 | 0.29 | | 0.23 | 0.20 |
| 90 [1327.5] | 0.68 | 0.60 | | 0.38 | 0.22 |
| 100 [1475] | 0.76 | 0.68 | 0.632 | 0.52 | 0.32 |
| 110 [1622.5] | 0.78 | 0.71 | | 0.56 | 0.40 |
| 120 [1770] | 0.79 | 0.76 | | 0.60 | 0.49 |

1 Bar = 14.75 PSI. [Density @ 31 C.° & 1070 psi [72.5 Bar] = 0.469 g/cc].

TABLE 7

Polymer Weight Loss during Gelation Reactions of Polyethylene [2M] Gels

| Preparation Date | Reaction Time, Minutes | Polymer weight loss Wt % | Initial Polymer solution Conc., Wt % | Final polymer solution Conc., Wt % | Dry Aerogel Density, g/cc |
|---|---|---|---|---|---|
| 5/14-15/ | 10 | 29.0 | 1.6 | 1.14 | 0.27 |
| 5/27/ | 10 | 20.0 | 1.6 | 1.28 | 0.4 |
| 6/2-4/ | 30 | 54.4 | 1.6 | 0.73 | 0.124 |
| 6/9-11/ | 30 | 61.4 | 1.6 | 0.62 | 0.11 |
| 6/16-18/ | 60 | 64.5 | 1.6 | 0.57 | 0.079 |

TABLE 8

Preparation of 2M MW Polyethylene Aerogels

| Preparation Date | Initial Polymer concentration, wt. % (final) | Maximum pressure in autoclave, psi | Aerogel Dimensions, cm | Aerogel Density, g/cc | Pore Volume, cc/g | Volume Porosity % | Remarks |
|---|---|---|---|---|---|---|---|
| 8/15-18/ | 0.9 (0.54) | 1500 | 3 sheets: 23.5-27 × 6.67-7.9 × 0.115-0.2 | 0.24-0.0485 | 23.6-40.83 | 96.0-98.0 | Acetone treatment |
| 8/23-25/ | 0.92 | 1450 | 4 sheets: 26.1-28 × 8.0-8.4 × 0.23-0.27 | 0.0245-0.032 | 30.4-34.9 | 97.3-98.0 | Acetone treatment |
| 9/13-15/ | 0.92 | 1650 | 26.9 × 9.8 × 0.24 | 0.032 | 31.425 | 97.42 | Acetone treatment |
| 9/19-20/ | 1.04 | 1700 | 4-sheets average; | 0.02 | 51.8 | 98.4 | No more acetone treatments. white, silky touch, static cling, good radiometric performance |
| 10/20/ | 0.95 | 1650-1700 | 36.3 × 29.3 × 0.33 | 0.0195 | 49.17 | 98.3 | First large sheet 12" × 15" |
| 11/8-10/ | 0.95 | 1700 | 32.5 × 26.7 × 0.448 | 0.02 | 49.17 | 98.3 | 13" × 10.7" sheet |
| 11/17/ | 0.95 | 1650 same day drying | 31.9 × 26.1 × 0.5 | 0.021 | 47.7 | 98.3 | Flawless sheet |
| 11/23-24/ | 0.67 | 1700 | Sample; 5.5 × 4.9 × 0.11 | 0.0236 | 41.54 | 98.0 | |
| 12/12/ | 0.67 (0.62) | 1700 | Sample; 7.5 × 3.0 × 0.134 | 0.0166 | 59.4 | 98.6 | Sheet tore to pieces |
| 12/13/ | 0.62 | 1700, same day | Sample; 2.8 × 4.8 × 0.19 | 0.012 | 82.5 | 99.0 | First record; not integral sheet, lots of holes |
| 1/04/ | 0.60 | 1600, same day | Sample; 6.4 × 3.8 × 0.28 | 0.021 | 47.7 | 98.3 | 4-holes in sheet |
| 1/10/ | 0.58 | 1700, same day | 22.5 × 30 × 0.35 | 0.013 | 73.5 | 98.9 | 9" × 12" sheet |
| 2/17/ | 0.29 | 1700, same day | Sample #2; 3.2 × 4.6 × 0.28; samples #1, 2, 4 | 0.0097 0.014-0.016 | 102.26 62-72 | 99.20 98.7-98.9 | Record porosity & density |

Encapsulation of Silica Aerogel Particles in Polyethylene Aerogel

Procedures:

Silica aerogel powder: silica alcogel was made by mixing silica alkoxide, water, and hydrofluoric acid catalyst at 45° C. The alcogel was micronized with a blender and sieved on 140 mesh [105 microns]. The micronized gel particles were dried by $CO_2$ supercritical method in an autoclave.

Encapsulation in polyethylene aerogel: 5 grams of 2 million MW polyethylene powder was dissolved in 630 ml hot toluene. Silica aerogel powder [80 ml] was mixed with the hot polyethylene toluene solution and 1.5-gram benzoyl peroxide catalyst was added to form gel solution. The gel solution was poured in a mold forming a thin layer of polyethylene gal enclosing the silica aerogel particles. On drying by $CO_2$ supercritical method, an aerogel sheet was obtained as shown in Table 9.

TABLE 9

Ultra Thin Sheets of Polyethylene (MW-2 million) Aerogel Encapsulating Silica Aerogel Particles (<100 mesh, 150µ) at 90% Volume Silica Aerogel to 10% Volume Polyethylene Aerogel

| Preparation Date | Thickness (mm) | Dimensions (L × W, cm) | Aerogel Density (g/cc) | Pore Volume (cc/g) | Volume Porosity (%) | Remarks |
|---|---|---|---|---|---|---|
| 8/2-23/ | 0.74 | 21 × 11 | 0.123 | 7.74 | 95.2 | Very good, flexible sheets encapsulating silica aerogel particles |

Radiometric and Electric Properties of Silica Aerogel-PE Aerogel Sheets:

These sheet wafers were tested for wide band antenna applications. The test results showed that the silica aerogel-PE aerogel wafer had a sheet resistance of 250 million Ohms per square. This is much [25 thousand to 50 thousand times] higher than previously obtained by other semiconductor resistors of 5-10 thousand ohms per square. This type of aerogel sheet wafers is very promising not only for thermal sensing the w-band and infra-red [thermal insulation], but also for its very high electric resistance [very low dielectric constant]. The silica aerogel-PE aerogel wafers also had refractive index, q, between 1.01-1.09 for the wavelength between 8-14 microns, and extinction coefficient, κ, between 0.0096-0.0104 for the same wavelength range.

EXAMPLES

Example-1

Preparation of Polyethylene [PE-2M] Aerogel Fiber Web 1400 ml anhydrous toluene was boiled in a reactor under reflux at 114 C.°, while mixing at 200 rpm. To boiling toluene, 1.5 grams polyethylene [PE-2M] in 50 ml toluene dispersion was added, and dissolved to a clear solution. To boiling polymer solution, a catalyst solution of 0.3 g benzoyl peroxide in 50 ml toluene, was added and mixing was resumed at 114 C.° for 55 minutes, after which, the hot gel solution was drained at a controlled rate onto the spin disc in toluene vapor saturated collection chamber/vessel which sprayed the fiber web onto a gel support sheet attached inside the up/down moving collection vessel. The gel-laden support sheet was removed from collection vessel, and placed in an autoclave, for supercritical extraction of toluene at 1700-1800 PSI and 32-34 C.°. The result aerogel fiber web was uniform sheet, about six feet long [1.8 meter], 8-9 inches wide, with no visible pinholes. The aerogel fiber web density was 0.01 gram/cc and 99.2% volume porosity. Repeats of this test showed density ranging from 0.0085-0.018 g/cc with corresponding volume porosity of 98.5% to 99.3%.

Example-2

Preparation of Chemically Resistant and Strengthened Polyethylene Aerogel Fiber Web with Polypropylene, Polyvinyl Acetate, Polyvinylidene Fluoride-CO-Hexafluoropropylene 2800 ml anhydrous toluene was boiled in a reactor under reflux at 114 C.° with mixing at 22 rpm. To boiling toluene, a dispersion of 0.45 g polypropylene [PP-0.3M] in 50 ml toluene, was added, followed by addition of 1.05 g polyethylene PE-2M+polyvinyl acetate [PVAc-0.5M] in 50 ml toluene. This was followed by addition of 0.45 g PVF-CO-HFP in 50 ml dimethyl acetate, and the temperature was raised to 120 C.°. To boiling clear solution a catalyst solution of 0.6 g benzoyl peroxide in 50 ml toluene was added, and mixing was continued for 15 minutes at 120 C.°. The hot solution was drained onto the spinning dice to form the fiber web, which was autoclaved at 1700-1899 PSI at 32-34 C.° to extract the toluene and produce aerogel fiber web.

The results showed a good uniform web, with a density of 0.02 g/cc, and volume porosity of 98.65%.

Example-3

Preparation of Air-Dried Chemically Resistant and Strengthened Polyethylene Fiber Web The same procedure and composition reported in Example 2 was used, except that polyvinyl acetate, was repeated, but using air drying instead of supercritical drying. The results showed a good aerogel web with a density of 0.052 g/cc, and porosity of 94.5%. The air-dried web was translucent/transparent and was thinner than supercritical-dried web, which was opaque and white.

Example-4

Preparation of Oil Repellant Aerogel Fiber Web by Coating with PEVA [Ethylene Vinyl Alcohol Copolymer] Gel Solution The polyethylene aerogel fiber web, which is water repellant, can also be made oil repellant by coating with PEVA gel solution. Thus, 1800 ml anhydrous toluene was boiled under reflux at 120 C.°, then polymer dispersion of 1.05 g polyethylene [PE-2M] and 0.45 g polypropylene was added to boiling toluene, followed by addition of 0.45 g PVF-CO-HFP in 50 ml dimethyl acetamide. To the clear polymer solution, 50 ml toluene containing 0.6 g benzoyl peroxide was added and mixing was continued for 15 minutes at 120 C.°. The hot gel solution was drained at a controlled flow rate onto the spinning disc for making the fiber web. The web was allowed to air dry before coating with PEVA solution.

Coating PEVA solution preparation: 1.0 g PEVA was dissolved in 100 ml Dimethyl Acetamide [DMAc] at 130 C under reflux, then 0.6 g benzoyl peroxide in 10 ml DMAc was added and mixing was continued for 15 minutes at 130 C.°. After cooling to ambient temperature, the gel solution was transferred to spray bottles.

Web Coating procedure: The aerogel fiber web was sprayed with PEVA gel solution to saturation; this is followed by acetone spray also to saturation. The wet coating was dried with a hot air dryer. The coating procedure may be repeated once more as required. The results were as follows: the web density=0.078 g/cc, porosity=94.14%; No attack or penetration/diffusion of the web by hydraulic or fuel oil or lubricating oil.

Example-5

Coating Aerogel Fiber Web with Nylon-12 Gel Solution

To 500 ml boiling DMAc at 140 C.° under reflux, add 10 grams of Nylon-12, followed by addition of catalyst solution of 6 grams of Benzoyl peroxide dissolved in 50 ml DMAc and mixing was continued for 20 minutes. After cooling, the solution was poured into a metal pan, where a sheet of previously prepared PE-2M aerogel fiber web was bathed/soaked for a few minutes, then removed and dried with a hot air dryer.

Example-6

Preparation of Polyethylene [PE-0.5M+PE-2M] Aerogel Fiber Web

To boiling 1400 ml anhydrous toluene, a dispersion of 1.05 g PE-0.5M+0.45 g PE-2M] in 50 ml toluene was added and dissolved. A catalyst solution of 0.3 g benzoyl peroxide in 50 ml toluene was added and mixed for 15 minutes at 120 C.°. Hot toluene was added into collection vessel to keep it warm and minimize any air-drying of gel. The hot gel solution was drained onto the spinning disc and the formation of fiber web cycle was initiated. The fiber web was autoclaved to remove the toluene and obtain dry aerogel fiber web sheet. The result showed a density of 0.01 g/cc, and porosity of 99.2%.

Example 7

Preparation of Transparent Aerogel Fiber Web

To boiling 2.5 liter of anhydrous toluene at 112-114 C.°, 3 grams of polyethylene [PE-0.5M] in 50 ml toluene was added and dissolved. The temperature of polymer solution was lowered to 100 C.° and the catalyst solution [1.2 g in 50 ml toluene, was added and mixed for 60 minutes. The solution was drained onto the spinning disc and fiber web making process was initiated. Excess toluene was removed from the bottom of collection chamber, and the fiber web gel was allowed to air-dry overnight.

The results showed that the aerogel web was almost transparent with light transmission across the web of 94.6%. The density was 0.122 g/cc, and porosity=89.84%. When the web was heat pressed at "silk" setting for 8 minutes, the light transmission increased to 96.2%. The density was 0.11 g/cc, with porosity=90.88%. For reference, light transmission of a clear glass slide was 96.6%.

Example 8

Preparation of Single Aerogel Fibers

To boiling 900 ml anhydrous toluene, a dispersion of 3.5 grams polyethylene [PE-2M] and 3.5 grams polyethylene [PE-0.5M] in 50 ml toluene, was added and mixing continued at 113° C. to a clear solution. A catalyst solution of 1.4 grams benzoyl peroxide in 50 ml toluene was added and mixing was continued for 5 minutes at 113° C. and 5 minutes without heating. The gel solution was poured into a metal pan and left to cool down to room temperature. 625 ml clear toluene liquid was decanted, and the rest of the gel solution was fed into a spin disc/cup of a cotton candy Floss machine, while spinning at 3500 rpm. Fiber gel filaments/fibers were observed to form and were left to air dry.

Example-9

Absorption-Capture of Bile and Fats with PE Aerogels & Aerogel Fiber Webs Leading to Reduction of Body Cholesterol Samples of PE-only aerogels, either fiber webs or molded sheets, prepared as described in earlier examples, were used for absorption-capture laboratory tests of bovine bile solution [6 grams of bovine bile powder dissolved in 94 ml water, at 37° C.], and canola cooking oil [representing food fats], and human bile absorption trials.

Laboratory tests at 37° C. indicated that up to 15.0 grams of bovine bile solution was absorbed-captured by 1.0 gram of PE aerogel, and up to 7.2 grams of canola oil was absorbed-captured by 1.0 gram of PE aerogel. Absorption kinetics of oil was much faster than absorption of bile solution, likely because the bile solution is water based. As noted later, PE aerogels are hydrophobic and do not absorb pure water.

Pristine™ "BILIPIDEX" Delivery System for Human Trial:

For this purpose, the PE-aerogel sheets were shredded with shearers/scissors into small shreds to fit into pharmaceutical grade gelatin capsules provided by Capsugel Company, at the dose of either 0.1 or 0.2 gram per capsule. The aerogel-loaded capsules were then coated with enteric [stomach acid resistant] coating using hydroxypropyl methylcellulose phthalate [HPMC]-acetone solution at 56° C., with a concentration of 5 grams HPMC in 100 ml acetone. Three thin coatings were sufficient to make these capsules acid insoluble [dilute HCL, pH 1.2-2.5, simulating stomach acid concentration], but readily soluble in slightly alkaline solution [pH 5.5-8.5] to simulate the small intestines and duodenum, where the capsule will deliver the aerogel, where absorption-capture of bile and excess fats would take place. For human trials, the change in body total cholesterol, was used as a measure and indication of the extent of human bile absorption-capture by PE aerogel, since bile capture and removal from the body, would stimulate the liver to manufacture more bile to make up for the lost bile. Bile is manufactured by the liver through reactions with body-stored cholesterol. The bile solution then is concentrated to about 6% wt. in the gall bladder, which injects the bile into the duodenum and small intestines, as commanded by the body to respond to assimilating fatty foods into the blood stream.

Results of Human Trials are shown below:

Human Trials of Pristina™-Bilipidex Pe-Aerogels

TABLE 10

[BILIPIDEX CONTAIED ONLY PE-0.5M AEROGEL; TRIALS 1&2, AEROGEL HAD 15 GRAMS BILE PER 1.0 GRAM AEROGEL ABSORPTION CAPACITY, FOR TRIAL #3, IT HAD 10 G BILE PER 1.0 G AEROGEL CAPACITY]

| Trial # | Total days | Average dose of BILIPIDEX, g/day | Cholesterol mg/dL Start | Cholesterol mg/dL End | Cholesterol mg/dL Reduction | Estimated % bile capture* | Remarks |
|---|---|---|---|---|---|---|---|
| 1 | 8 | 0.65 | 193 | 165 | 28 | 9.75 ml/33% | Low fat diet |
| 2 | 7 | 0.65 | 165 | 120 | 45 | 9.75 ml/33% | Low fat diet |
| 3 | 12 | 1.0 | 193 | 138** | 55 | 10 ml/33.33% | High fat diet |

*Based on 30 ml concentrated gall bladder bile secretion per day at 6% wt.
**Cholesterol measured 3 days after trial at 173 mg/dL, while on high fat diet; Estimated Cholesterol at end of 12 day trial = 12/15 × 173 = 138 mg/dL.

Effect of Bilipidex Aerogel on Weight Loss:

Weight loss was not directly related to cholesterol reduction, as Bilipidex-Aerogel addresses only the fatty components contributing to body weight. The weight fluctuated during the period of trials, but generally declined by almost five (4.5-5.0) pounds (~2 Kg) over the 2-3 months period of intermittent consumption of the aerogel capsules.

Thermal Conductivity of Polyethylene [Pe-0.5M] Aerogel Fiber Web

Thermal insulation is measured by the thermal conductivity factor: k in milli-Watts per meter thickness per degree kelvin)(K.°); thus, the lower thermal conductivity factor [k], the higher is the insulation performance. Measured thermal conductivity of some PE-0.5M aerogel fiber webs are shown below:

2-layer web: k (mW/m*K.°)=14.63 at 21 C.°; and 20.22 at 24 C.°.

3-layer web: k (mW/m*K.°)=9.16 at 8 C.°; 10.44 at 18 C.°; 17.3 at 23 C.°; 22.7 at 26 C.°.

Absorption Capacity of Polyethylene [Pe-0.5M] Aerogel Fiber Web: Laboratory Tests Showed that:

7.2 grams of cooking oil can be absorbed/adsorbed by 1.0 gram of PE-0.5M aerogel fiber web.

15.0 grams of bile solution can be absorbed by 1.0 gram of PE-0.5M aerogel fiber web.

No absorption of pure water.

Aqueous solutions of soaps/detergents also should be absorbed by polyethylene aerogel fiber web.

Encapsulation of Particulates and Substances by Aerogel Fiber Web

Several types of particulates have been successfully encapsulated in the PE-aerogel fiber web, with no dusting. Encapsulated particulates include nano-sized diamonds, silica aerogel, Pristina™ Tri-cat Aerogel Catalyst, and Pristina™ ST-31 Adsorbent. Other substances also should be successfully encapsulated in the aerogel fiber web.

I claim:

1. Method for making a polymer aerogel product or copolymer aerogel product, which comprises the steps of:
   (a) forming a polymer cross-linked gel solution or copolymer cross-linked gel solution in the presence of a polymer catalyst and solvent therefor or copolymer catalyst and solvent therefor;
   (b) draining the polymer cross-linked gel solution or copolymer cross-linked gel solution onto a spinning disk or cup for forming a fiber web; and
   (c) collecting the polymer fiber web or copolymer fiber web produced from the spinning disk or cup; and
   (d) removing the solvent from the polymer fiber web or copolymer fiber web produced in step (c) under aerogel forming conditions to form the polymer aerogel product or copolymer aerogel product.

2. The method of claim 1, wherein the spinning disk or cup was spinning at a rate of at least 3,000 rpm.

3. The method of claim 1, wherein the polymer or copolymer aerogel fiber web is made to different widths through spraying with a controlled up and down motion.

4. The method of claim 3, wherein the polymer fiber web or copolymer fiber web produced in step (c) is distributed from the spinning disk or up onto a collection vessel that moves up and down motion wherein the vertical up and down motion is controlled by a motion sensor and actuator.

5. The method of claim 1, wherein the solvent is removed by one or more of air-drying, autoclaving, or supercritical drying.

6. The method of claim 1, wherein the dried the polymer aerogel product or copolymer aerogel product is converted into a yarn by twisting the polymer aerogel product or copolymer aerogel product.

7. The method of claim 6, wherein the yarn is formed by twisting with a spindle technique.

8. The method of claim 1, which is repeated to produce multiple polymer fiber webs or copolymer fiber webs to form a three-dimensional structure.

9. The method of claim 1, wherein the polymer or copolymer is one or more of a polyolefin, a polyester, or a polyamide.

10. The method of claim 1, wherein the polymer or copolymer aerogel product has therein encapsulated particulates.

11. The method of claim 1, additionally comprising the step of coating the polymer aerogel product or copolymer aerogel product with one or more of polypropylene, polyvinyl acetate, polyvinylidene fluoride-co-hexafluoropropylene, ethylene vinyl alcohol copolymer, polyamide, or polyester.

12. The method of claim 1, wherein the polymer or copolymer aerogel product is encapsulated in enteric capsules, wherein the capsules are coated with an enteric coating, said enteric-coated aerogel capsules being effective in absorbing lipids and bile in situ.

13. The method of claim 1, additionally comprising the step of absorbing oil with the polymer aerogel product or copolymer aerogel product.

14. The method of claim 1, additionally comprising the step of coating the polymer aerogel product or copolymer aerogel product with an oil resistant coating for making a water repellant and oil repellant aerogel material.

15. The method of claim 1, wherein the collected polymer or copolymer aerogel fiber web or yarn measures between at least about 1.5 m and about 25 cm and has a thickness of between about 0.1 mm and about 10 mm.

16. The method of claim 1, additionally comprising the step of forming the collected polymer aerogel product or copolymer aerogel product into one or more products for thermal insulation, acoustic insulation, electric insulation, absorbent, encapsulation, separation membrane, controlled release, or tissue scaffold.

17. The method of claim 1, additionally comprising the step of weaving the collected polymer aerogel product or copolymer aerogel product into a fabric.

\* \* \* \* \*